(12) United States Patent
Shaheen et al.

(10) Patent No.: US 11,419,833 B2
(45) Date of Patent: Aug. 23, 2022

(54) NASALLY ADMINISTERED PHARMACEUTICAL COMPOSITION FOR THE TREATMENT OF EPILEPSY AND RELATED DISORDERS

(71) Applicants: Farzana Shaheen, Karachi (PK); Atta-ur Rahman, Karachi (PK); Muhammad I. Choudhary, Karachi (PK); Shabana U. Simjee, Karachi (PK); Zehra Batool, Karachi (PK)

(72) Inventors: Farzana Shaheen, Karachi (PK); Atta-ur Rahman, Karachi (PK); Muhammad I. Choudhary, Karachi (PK); Shabana U. Simjee, Karachi (PK); Zehra Batool, Karachi (PK)

( * ) Notice: Subject to any disclaimer, the term of this patent is extended or adjusted under 35 U.S.C. 154(b) by 0 days.

(21) Appl. No.: 17/014,744

(22) Filed: Sep. 8, 2020

(65) Prior Publication Data
US 2021/0322344 A1 Oct. 21, 2021

Related U.S. Application Data

(63) Continuation-in-part of application No. 16/849,804, filed on Apr. 15, 2020, now abandoned.

(51) Int. Cl.
| | | |
|---|---|---|
| *A61K 31/192* | (2006.01) |
| *A61K 38/05* | (2006.01) |
| *A61K 47/64* | (2017.01) |
| *A61K 31/16* | (2006.01) |
| *A61K 9/00* | (2006.01) |
| *A61K 47/26* | (2006.01) |
| *A61K 47/44* | (2017.01) |
| *A61P 25/08* | (2006.01) |

(52) U.S. Cl.
CPC ............ *A61K 31/16* (2013.01); *A61K 9/0043* (2013.01); *A61K 31/192* (2013.01); *A61K 38/05* (2013.01); *A61K 47/26* (2013.01); *A61K 47/44* (2013.01); *A61K 47/64* (2017.08); *A61P 25/08* (2018.01)

(58) Field of Classification Search
CPC .... A61K 9/0043; A61K 31/192; A61K 38/05; A61K 47/64; A61P 25/08; A61P 25/10; A61P 25/12; C07K 5/0686; C07C 57/26
See application file for complete search history.

(56) References Cited

U.S. PATENT DOCUMENTS

| | | | |
|---|---|---|---|
| 2008/0004353 A1* | 1/2008 | Rahman | C07C 45/004 514/690 |
| 2015/0148417 A1* | 5/2015 | Rahman | C07C 57/26 514/557 |
| 2017/0348276 A1* | 12/2017 | Bryson | A61P 25/00 |
| 2019/0290598 A1* | 9/2019 | Rahman | A61P 25/28 |

\* cited by examiner

*Primary Examiner* — Jeffrey E. Russel
(74) *Attorney, Agent, or Firm* — Sarfaraz K. Niazi

(57) ABSTRACT

A nasally administered liquid, including suspension and viscous liquid compositions, containing a therapeutically effective quantity of (Z)-2-(3,5,5-trimethyl-2-cyclohexen-1-ylidene) acetic acid, its salts or analogs, combined with suitable pharmaceutical ingredients, to treat epilepsy.

2 Claims, 19 Drawing Sheets

NASALLY ADMINISTERED PHARMACEUTICAL COMPOSITION FOR THE TREATMENT OF EPILEPSY AND RELATED DISORDERS

CROSS REFERENCE TO RELATED APPLICATION

This application is a continuation-in-part of U.S. patent application Ser. No. 16/849,804 entitled NASALLY ADMINISTERED PHARMACEUTICAL COMPOSITION FOR THE TREATMENT OF EPILEPSY AND RELATED DISORDERS, filed on Apr. 15, 2020, the contents of which are incorporated herein by reference in its entirety.

FIELD OF THE INVENTION

The present invention is directed to pharmaceutical composition containing (Z)-2-(3,5,5-trimethyl-2-cyclohexen-1-ylidene) acetic acid for nasal administration, methods of manufacture and their uses in neurological disorder especially epilepsy. According to the present invention, nasal pharmaceutical composition containing (Z)-2-(3,5,5-trimethyl-2-cyclohexen-1-ylidene) acetic acid and its analog can be used to treat CNS disorders, such as epilepsy, pain, anxiety, spasticity and migraine.

The nasal pharmaceutical composition containing (Z)-2-(3,5,5-trimethyl-2-cyclohexen-1-ylidene) acetic acid of the present invention are suspensions or viscous liquid pharmaceutical compositions, namely, creams, gels and emulsions, that are formulated with therapeutically effective amounts of (Z)-2-(3,5,5-trimethyl-2-cyclohexen-1-ylidene) acetic acid, and are nasally administered to treat epilepsy disorder.

BACKGROUND OF THE INVENTION

Neurological diseases, such as epilepsy, Parkinson's disease, multiple sclerosis, Alzheimer's disease, chronic age-related neurodegenerative diseases, are associated with changes in neural functions and the burden of these diseases is increasing globally with high healthcare costs. Epilepsy is a major neurological disorder globally with high prevalence in developing world.

Currently available chemotherapeutic agents are not capable of curing the seizures completely and in majority cases, epileptic patients have to rely on medication to control seizures throughout their life, while, most drugs have severe side-effects. In view of the large percentage of uncontrolled epileptics and the side effects experienced by patients with the existing medications, there is an urgent need for more selective and less toxic anticonvulsant drugs.

Nasal administration is an appropriate method for systemic delivery of drugs due to several advantages, such as large surface area of nasal mucosa, rapid initiation of action comparable to injection/oral administrations, lower chances of enzymatic degradation compared with GI tract and by pass the first pass metabolism in the liver. Important aspect of nasal administration is that, some amount of drug can directly deliver through olfactory neurons into the brain tissues or cerebrospinal fluid which provide better treatment for central nerves system diseases. For example, zolmitriptan (U.S. Pat. No. 5,466,699A) was developed to treat migraine; it was then commercially available as a nasal spray formulation (U.S. Pat. No. 6,750,237). Procedures for nasal administration of drugs are reported in literature, for example, an oil based vehicle for testosterone is described in U.S. patent application Ser. No. 13/194,928 and Application No. PCT/IB2012/001127. Drugs with poor solubility are difficult to be developed into a formulation for nasal administration and they require suitable solvent with surfactant to increase the absorption of drugs through nasal route. Therefore, the use of suitable vehicle for nasal administration of drugs with no toxicity to the nasal mucosae is desirable. However, there is no correlation available to assure that a particular class of drugs will be more suitable for nasal administration, nor is there any data to show the teaching to test a drug for a particular treatment.

Statistical significance was obtained by one-way ANOVA followed by Bonferroni post-hoc test **p<0.01 as compared control animals; ++p<0.01 as compared PTZ group.

Figure 14:
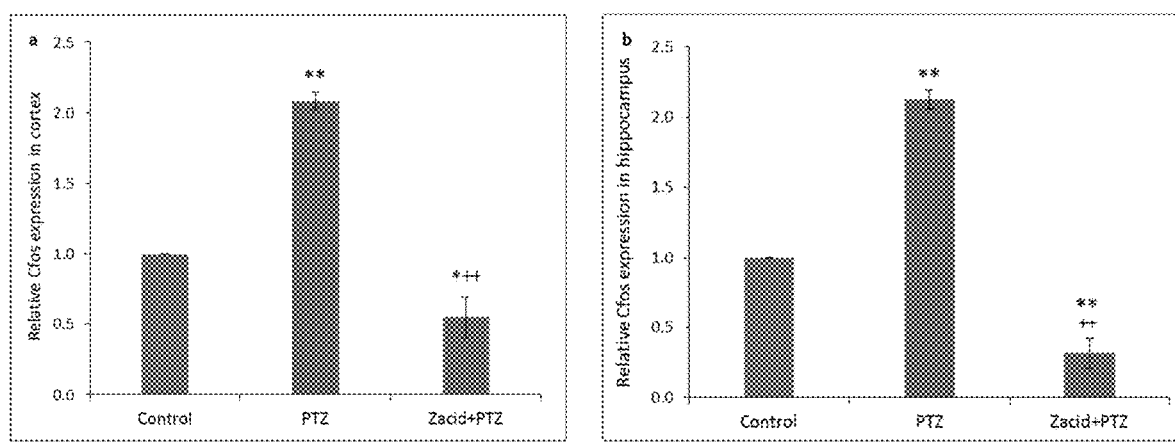

FIG. 14 Effects of intranasal administration of Z-acid formulation and diazepam on gene expression of c-fos in PTZ-induced rat model of acute seizure observed in cortex (a) and hippocampus (b). Values are mean±SEM (n=3). Statistical significance was obtained by one-way ANOVA followed by Bonferroni post-hoc test *p<0.05, **p<0.01 as compared control animals; ++p<0.01 as compared PTZ group.

Figure 15:
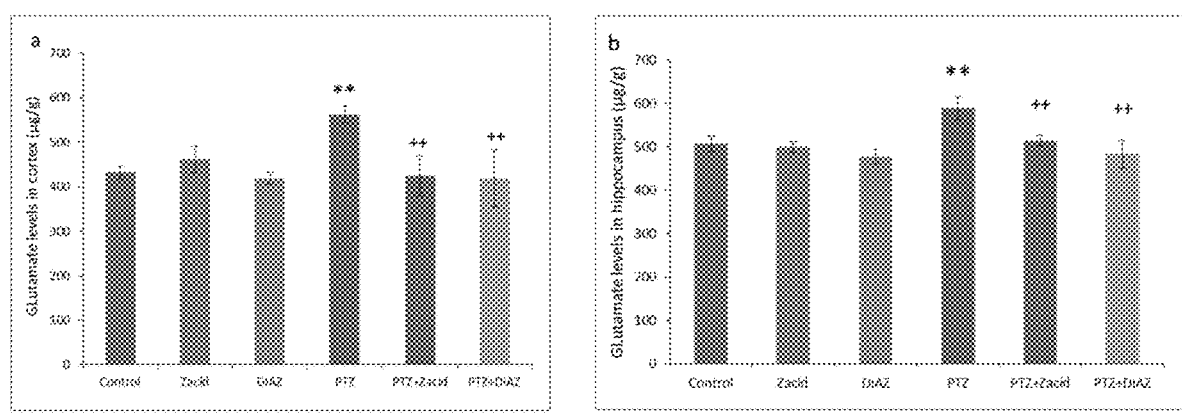

FIG. 15 Effects of intraperitoneal administration of Z-acid and diazepam on glutamate levels in PTZ-induced rat model of acute seizure observed in cortex (a) and hippocampus (b). Values are mean±SD (n=6). Statistical significance was obtained by two-way ANOVA followed by Bonferroni post-hoc test **p<0.01 as compared control animals; ++p<0.01 as compared PTZ group.

Figure 16:
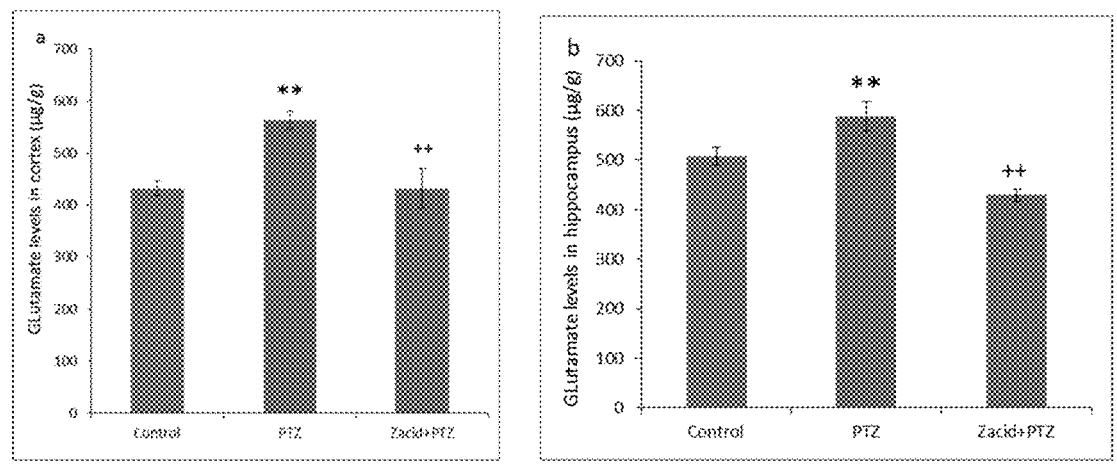

FIG. 16 Effects of intranasal administration of Z-acid formulation on glutamate levels in PTZ-induced rat model of acute seizure observed in cortex (a) and hippocampus (b). Values are mean±SD (n=6). Statistical significance was obtained by two-way ANOVA followed by Bonferroni post-hoc test **p<0.01 as compared control animals; ++p<0.01 as compared PTZ group.

Figure 17:
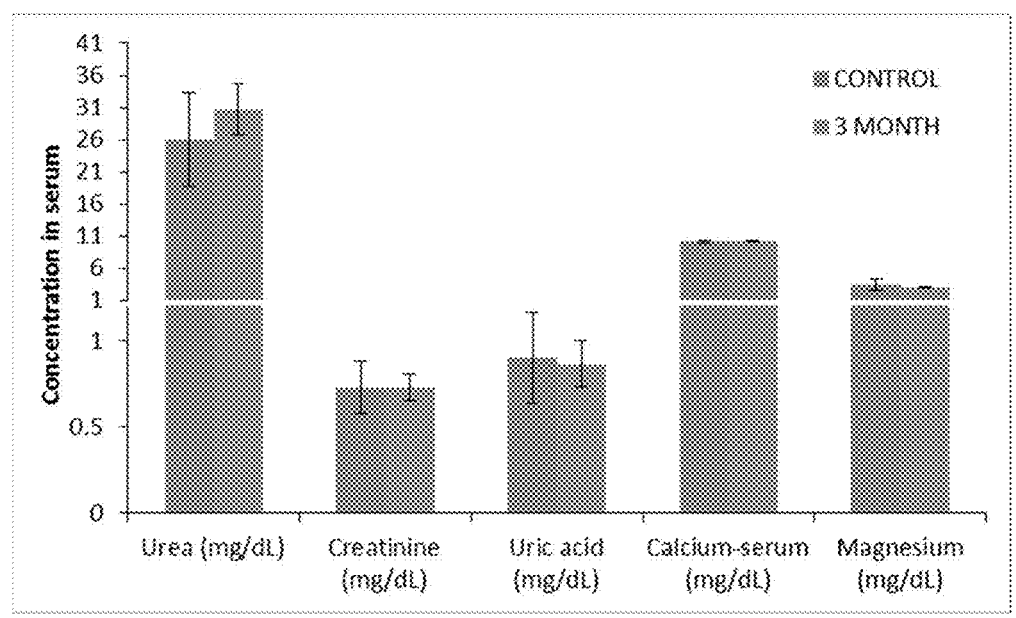

FIG. 17 Pictorial representation of kidney profile, calcium and magnesium in rat serum after administration of Z-acid Formulation I (50 mg/kg, intra-nasal) for 3 months.

Figure 18:
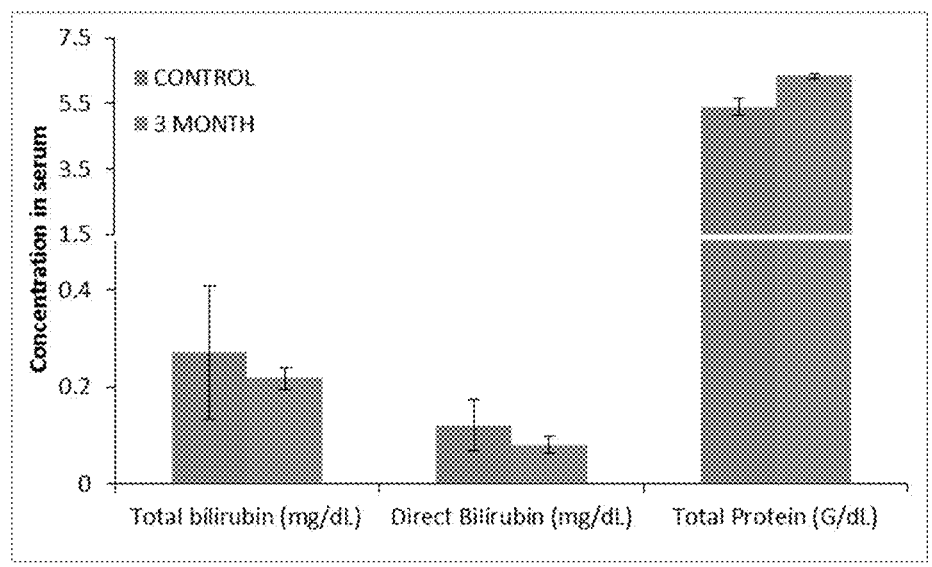

FIG. 18 Pictorial representation of bilirubin and protein in rat serum after administration of Z-acid Formulation I (50 mg/kg, intra-nasal) for 3 months.

Figure 19:
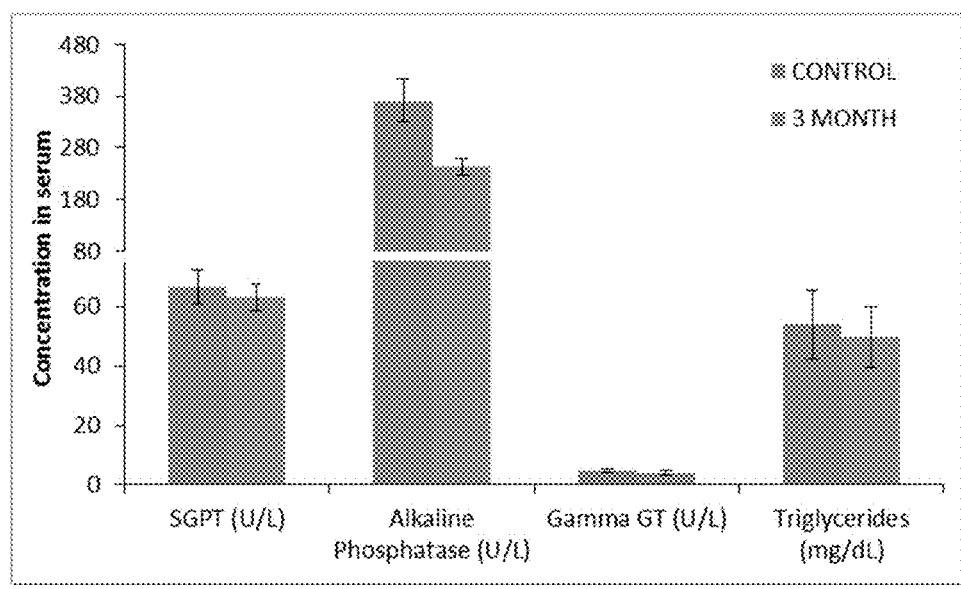

FIG. 19 Pictorial representation of liver profile and tri-glycerides in rat serum after the administration of Z-acid Formulation I (50 mg/kg, intra-nasal) for 3 months.

DESCRIPTION OF PRESENT INVENTION

The current invention is directed towards nasal delivery of (Z)-2-(3,5,5-trimethyl-2-cyclohexen-1-ylidene) acetic acid in form of pharmaceutical composition containing oils and surfactants. The instant invention is a nasal formulation of (Z)-2-(3,5,5-trimethyl-2-cyclohexen-1-ylidene) acetic acid that showed a ten-fold improvement in the activity of the compound that was surprising when compared with intraperitoneal administration. After establishing the anticonvulsant and antiepileptic activities of (Z)-2-(3,5,5-trimethyl-2-cyclohexen-1-ylidene) acetic acid, we developed a nasal formulation of the test compound. This formulation was applied through nasal route in different doses. Interesting observation was made at the dose of 50 mg/kg (body weight) of active compound, the nasal delivery of formulation was active enough to block the PTZ induced epileptiform activity in rats (since the animals in our test group were in the range of 200-210 g). The sub-chronic toxicity testing was performed for intraperitoneal administration of Z-acid and nasal application of Z-acid formulation in rats for a period of 3 months. At the end of the study, samples were processed and gross anatomical observations were made after sacrificing the animals. We did not find any sign of toxicity in the treated animals.

Syntheses of anticonvulsant (Z)-2-(3,5,5-trimethyl-2-cyclohexen-1-ylidene) acetic acid The syntheses of an anticonvulsant isomeric mixture of (E/Z)-2,2'-(3,5,5-trimethyl-2-cyclohexen-1-ylidene) acetic acid was carried out through hydrolysis of an isomeric mixture of E/Z ester 2 (scheme-1). The E/Z isomeric mixture of acid analog of isoxylitones was poorly soluble in water, E/Z isomeric mixture was characterized by spectroscopic studies (U.S. patent application Ser. No. 14/609,211).

Scheme-1: Synthesis of (Z)-2-(3,5,5-trimethyl-2-cyclohexen-1-ylidene) acetic acid

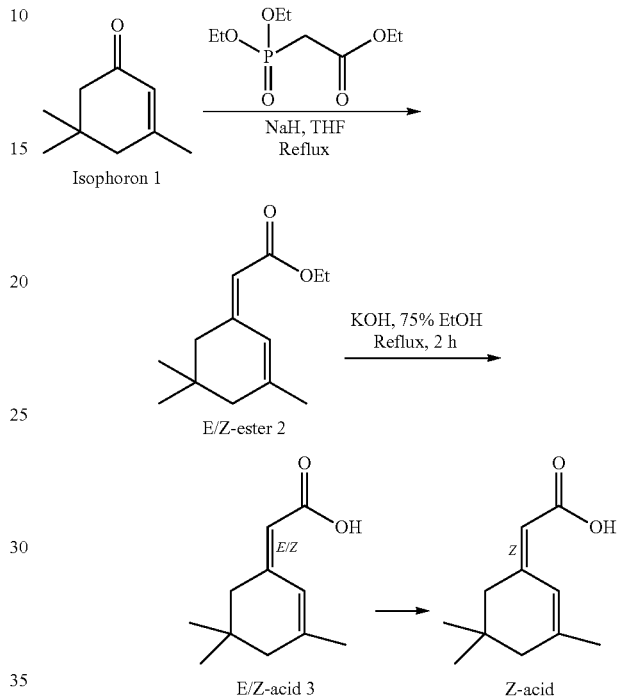

Pure isomeric (Z)-2-(3,5,5-trimethyl-2-cyclohexen-1-ylidene) acetic acid was obtained in pure form from recrystallization of E/Z-mixture of acid (Scheme-1) and it was characterized by spectroscopic studies.

In the present invention, detailed anticonvulsant activities of pure (Z)-2-(3,5,5-trimethyl-2-cyclohexen-1-ylidene) acetic acid (Z-acid) are described and nasal application of (Z)-2-(3,5,5-trimethyl-2-cyclohexen-1-ylidene) acetic acid in form of pharmaceutical composition was developed to inhibit PTZ-induced seizures. The purity of sample of Z-acid was checked under different chromatographic conditions and by $^1$HNMR from each batch of synthesis before performing any pharmacological testing. The pure Z-acid was found stable in different organic solvents at room temperature and even at high temperature. It was found stable under all conditions used in various experiments.

Synthesis of New Analogs of Isoxylitones

Scheme2: Synthesis of peptide analogs of Z-acid

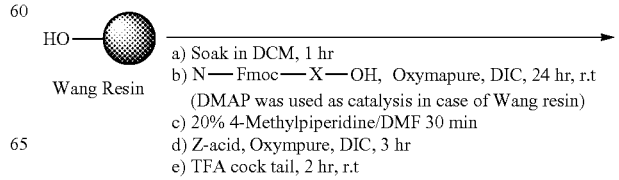

a) Soak in DCM, 1 hr
b) N—Fmoc—X—OH, Oxymapure, DIC, 24 hr, r.t
   (DMAP was used as catalysis in case of Wang resin)
c) 20% 4-Methylpiperidine/DMF 30 min
d) Z-acid, Oxympure, DIC, 3 hr
e) TFA cock tail, 2 hr, r.t -continued

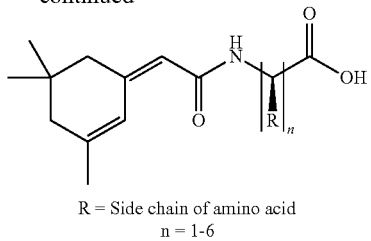

R = Side chain of amino acid
n = 1-6

Serine, Glycine and Lysine and gamma amino butyric acid were conjugated with Z-acid to develop more new analogs (Scheme2). Among these analogs, Z-acid-Lys-Lys-OH was water soluble and it was found active through nasal route.

Formulations

For testing, the Z-acid, the following formulations were compounded as viscous suspensions:

Formulation 1
Z-acid, 20 g, Canola Oil Qs to 100 mL
Formulation 2
Z-acid 20 g, Olive Qs to 100 mL
Formulation 3
Zacid 20 g, Tween 2 g, Olive oil Qs to 100 mL
Formulation 4
Zacid 20 g, Glycerin 5 g, Olive oil Qs to 100 mL Administration Z-acid formulation was administered through intranasal route in rats injected with slight anesthesia for EEG recording. Z-acid formulation was administered at the dose of 50 mg/kg therefore pharmaceutical composition of Z-acid for one rat (~200 g) was 10 mg Z-acid. For each formulation we observed same results with 100% efficacy for acute PTZ-induced epileptiform.

Pharmacological Screening

The screening of compounds was carried out both in acute seizure model (anticonvulsant activity) and chronic seizure model (anti epileptogenesis activity). The kindling model of epilepsy is considered to be a chronic model of epilepsy, which is primarily used for evaluating the test drug for anti-epileptogenic activity. The PTZ test is most commonly used in the primary screening for new antiepileptic drugs (AEDs). In the current study, acute model of scPTZ-induced seizure and kindling model of epilepsy was initially used to evaluate the anticonvulsant and anti-epileptic activity of Z-acid. Once established, we next moved to evaluate the activity of the Z-acid and its analog on the EEG pattern of epileptiform activity in brain of live animals through intraperitoneal and nasal routes. The toxicity profile of Z-acid was also studies for a period of 3 months both through intraperitoneal administration and nasal application.

Experimental Details

Z-acid and its various analogs were tested in acute PTZ-induced seizure model in mice. Each batch of the freshly synthesized Z-acid analog was evaluated for anticonvulsant activity in acute test in order to confirm the reproducibility.

In Vivo Subcutaneous PTZ-Induced Seizure Test in Balb/c Mice

All experimental procedures were performed in accordance with the NIH guidelines for the care and use of laboratory animals (NIH Publication No. 85-23 Rev. 1985) and it was further approved by the Advisory Committee on Animal Standards of International Center for Chemical and Biological Sciences (ICCBS), University of Karachi (Protocol #2019-013). Male NMRI or Balb/c albino mice weighing 19-25 g were housed in an environmentally regulated room on a 12:12 h light and dark cycle with 21±1° C. and had free access to food and water.

Anticonvulsant effects of the test compounds were evaluated using subcutaneous PTZ-induced seizure test (subcutaneous PTZ). PTZ was prepared in saline whereas Z-acid was dissolved in 0.1 N NaOH. The Z-acid and its analogs were administered intraperitoneally at least 30 min before subcutaneous administration of convulsive dose of PTZ (110 mg/kg). Following PTZ administration, animals were observed for at least 1 hour for the presence or absence of different types of seizure patterns i.e., onset of body twitches, threshold seizures, generalized seizures with loss of righting reflex, loss of righting reflex with tonic forelimb seizures, loss of righting reflex with tonic forelimb and hind limb seizures. Latency to PTZ-induced threshold seizures was also calculated. The latency to threshold seizure is defined as the interval between the time of the PTZ-injection and the occurrence of first episode of threshold seizure. Protection of testing material against PTZ-induced mortality within 24 hours was also evaluated. In all experiments, diazepam (7.5 mg/kg intraperitoneal) and valproic acid (100 mg/kg) were used as standard drug control.

PTZ-Induced Kindling (Anti-Epileptogenic Activity) in NMRI Mice:

The chemical kindling was induced according to the modified method of De Sarro i.e. by repeated treatment of mice with sub-convulsive dose of pentylenetetrazole (subcutaneous, 50 mg/kg) on alternate days. Four doses of Z-acid (150 mg/kg/day, 200 mg/kg/day, 250 mg/kg/day, and 300 mg/kg/day) were administered daily (intraperitoneal). However, on the day of PTZ administration, animals were treated with the Z-acid 30 minutes before administering PTZ. After PTZ was injected, each animal was placed separately in a clear plexiglass cage for close observations for 1 hour. The drug control groups received daily valproic acid. The Racine scoring categorization of epileptic seizures pattern was used to monitor the animals (Table 1). The animals showing score 4-5 were considered to be fully kindled. The cumulative kindling score was then calculated. Experiments were terminated once the animals were fully kindled. The treatment regimen is shown in table 2. At the end of each experiment, animals were humanely sacrificed.

TABLE 1

Behavioral rating scale for PTZ-induced epileptogenesis (Racine, 1972)

| Seizure Stages (1-5) | Seizure Patterns |
| --- | --- |
| 0 | No response |
| 1 | Ear & Facial Twitching |
| 2 | Convulsive wave through the body |
| 3 | Myoclonic jerks |
| 4 | Clonic-tonic convulsions, turn over into side position |
| 5 | Generalized clonic-tonic seizures, turn over into back position |

TABLE 2

Treatment groups of scPTZ-induced chemical kindling model of epileptogenesis

| Groups | No. of Animals | Treatment | Dose | Route of Administration |
|---|---|---|---|---|
| I (Normal Control) | 6 | Saline | 2 ml of 0.9% | intraperitoneal |
| II (Disease Control) | 6 | PTZ only | 50 mg/kg | subcutaneous |
| III (Test group 1) | 6 | Z-acid + PTZ | 150 mg/kg + 50 mg/kg | intraperitoneal + subcutaneous |
| IV (Test group 2) | 6 | Z-acid + PTZ | 200 mg/kg + 50 mg/kg | intraperitoneal + subcutaneous |
| V (Test group 3) | 6 | Z-acid + PTZ | 250 mg/kg + 50 mg/kg | intraperitoneal + subcutaneous |
| VI (Test group 4) | 6 | Z-acid + PTZ | 300 mg/kg + 50 mg/kg | intraperitoneal + subcutaneous |
| VII (Drug Control 1) | 6 | Diazepam + PTZ | 7.5 mg/kg + 50 mg/kg | intraperitoneal + subcutaneous |
| VIII (Drug Control 2) | 6 | Valproate + PTZ | 400 mg/kg + 50 mg/kg | intraperitoneal + subcutaneous |

Acute Neurotoxicity

The manifestation of neurotoxicity of Z-acid was determined by inverted screen acute neurotoxicity test. A platform of a rectangular metal screen was inverted through an arc of 180° was employed in our study. Mice were pre-tested on the apparatus the day preceding the experiment, and those failing the task were not used for the subsequent drug test. Testing was carried out at 5-, 30-, 60- and 120-minutes following intraperitoneal administration of Z-acid. Mice unable to climb to an upright position for 1 min duration were rated as failures.

Acute Behavioral Assessment

Animals were transferred into individual cages the day before the experiments to allow them to acclimatize to the new environment. The toxicity profiles were established by slightly modifying the procedure of Irwin as described by Turner, 1972. The behavior (locomotion, head weaving, biting, licking or grooming, hyper excitability, ataxia and sedation, writhing, jumping etc. of the animals were observed for 1-2 hr. after they were injected with vehicle, standard drug and test samples. These effects on behavior were recorded using a scoring system (scores were allocated according to the intensity of the symptoms from 0-4).

Muscle Relaxant Activity

This was examined by Traction test. The forepaws of a mouse were placed on a small twisted wire rigidly supported above a bench top. Normal mice grasped the wire with forepaws and when allowed to hang free, placed at least one hind foot on the wire within 5 seconds. Inability to put up at least one hind foot constituted failure to the traction. The test was conducted at 30 min and 1 h after the injection of saline, diazepam, valproic acid or Z-acid.

Gross Anatomy

Once the animals were observed for behavioral analysis, they were anesthetized, dissected and the gross anatomy of internal organs such as kidneys, liver, spleen, pancreas and heart were closely observed in order to see if there were any possible changes in the gross appearance of these organs.

Sub-Chronic Toxicity Profile:

To evaluate the sub-chronic toxicity profile of Z-acid the compound was administered daily into mice at the dose of 300 mg/kg (intraperitoneal) for a period of 3 months. The animals were divided into 5 groups (8 per group) as outlined below:

Group I normal control;
    Group II treated daily for 1 week;
    Group III treated daily for 2 weeks;
    Group IV treated daily for 1 month;
    Group V treated daily for 2 months;
    Group VI treated daily for 3 months At the end of the study, animals were anaesthetized, dissected and gross examination of vital organs were performed, along with serum and whole brain samples collection. Serum and brain sample were stored in −20° C. for further examination.

Pharmacokinetic Profile

The pharmacokinetics of Z-acid in both plasma and brain after a single intraperitoneal dose of Z-acid (300 mg/kg) was studied in mice. Animals were sacrificed at 5 min, 15 min, 30 min, 60 min, 120 min, 180 min, and 240 min after the dose administration (n=4 for each time point). Blood samples were obtained in heparin containing vacutainers. The control group consists of the animals receiving no other treatment and this serve as blank plasma and aided in optimization and validation of the GC/MS method. The blood samples were later centrifuged to obtain plasma which was stored at −20° C. for further processing. Likewise, the brain samples were also collected from the sacrificed animals and stored at −20° C. for further processing on GC-MS.

The pharmacokinetics of Z-acid formulation in both plasma and brain was also studied after a single nasal dose of Z-acid (50 mg/kg) in rat. Animals were sacrificed at 5 min, 15 min, 30 min, 60 min, 75 min, 90 min, 120 min and 180 min after the dose administration (n=4 for each time point). Blood samples were obtained in heparin containing vacutainers. The control group consists of the animals receiving no other treatment and this serve as blank plasma. The blood samples were later centrifuged to obtain plasma which was stored at −20° C. for further processing. Likewise, the brain samples were also collected from the sacrificed animals and stored at −20° C. for further processing on UPLC.

The pharmacokinetics of Z-acid formulation in plasma was also studied after a single nasal dose of Z-acid (50 mg/kg) in rabbits. Blood sample was collected after 15 min, 30 min, 60 min, 120 min and 180 min of dose administration (n=4). Blood samples were obtained in heparin containing vacutainers. The control group consists of the animals receiving no other treatment and this serve as blank plasma. The blood samples were later centrifuged to obtain plasma which was stored at −20° C. for further processing on UPLC.

PTZ-Induced Epileptiform Activity in Rats Followed by Intraperitoneal Administration of Z-Acid (EEG Protocol)

In this set of experiment, effect of Z-acid was investigated on PTZ-induced epileptiform activity. Rats (210±10 g) were divided into six groups as control, diazepam, Z-acid, PTZ, PTZ+diazepam, PTZ+Z-acid with 6 sample size in each group. PTZ was injected at the dose of 100 mg/kg. Z-acid was intraperitoneally injected in anesthetized rats at the dose of 150 mg/kg whereas drug control group was treated with 5 mg/kg dose of diazepam. Saline was used as placebo. PTZ was prepared in saline whereas Z-acid was dissolved in 0.1 N NaOH. EEG was recorded from cortical region of the rat brain.

The protocol was started by anesthetizing rat followed by fixing the animal in stereotaxic apparatus for surgery. The skin was removed to expose the bregma and lambda region of the skull. Three holes of 0.6 mm diameter were drilled with the help of a manual drill. One hole was made on the parietal lobe for the placement of active electrode whereas two were made on the occipital lobes for reference and ground electrodes. A screw with the length of 5 mm and diameter of 0.5 mm was inserted on each hole and electrodes were then connected with the EEG recording system. The recording was started by monitoring the baseline EEG recording for 5 min. After 5 min of noise-free recording, PTZ was injected to induce acute seizures. The EEG recording after the injection of PTZ was continued for 10 min to observe the induction of epileptiform activity. During this duration, spikes which are known as epileptiform were observed with high amplitude which was synchronized with seizures observed phenotypically in rat. After 10 min of recording, Z-acid was injected intraperitoneally to observe its effects on PTZ-induced epileptiform activity.

PTZ-Induced Epileptiform Activity in Rats Followed by Intranasal Application of Z-Acid Formulation (EEG Protocol)

In this set of experiment effects of Z-acid formulation was investigated on PTZ-induced epileptiform activity through nasal route of administration. Rats (210±10 g) were divided into three groups as control, PTZ and PTZ+Z-acid with 6 sample size in each group. PTZ was injected at the dose of 100 mg/kg. Z-acid formulation was administered through intranasal route in anesthetized rats at the dose of 50 mg/kg. Pharmaceutical formulations (1-4) were initially tested and we observed same results for all formulations. Z-acid-Lys-Lys-OH dissolved in water was tested through nasal route. EEG was recorded from cortical region of the rat brain.

The protocol for the preparation of the animals for treatment was same as described above. The nasal application of Z-acid formulation was done 30 min before PTZ injection. The recording was started by monitoring the baseline EEG recording for 5 min. After 5 min of noise-free recording, PTZ was injected to induce acute seizures in rat. The EEG recording after the injection of PTZ was continued to observe the induction of epileptiform. During this duration, spikes which are known as epileptiform were observed with high amplitude which was synchronized with seizures observed phenotypically in rat. Data was analyzed by one-way ANOVA with followed by Tukey's post-hoc analysis. Values $P<0.05$ were considered as significant.

Effects of Z-Acid Formulation I on BDNF and Cfos Gene Expression on PTZ-Induced Acute Seizure in Rats Rats were decapitated after recording the EEG to collect the brain samples. Cortex and hippocampus regions of brain were excised out to conduct analysis of gene expression using qRT-PCR. The tissue samples were processed for RNA isolation followed by synthesis of cDNA using Revert Aid First strand cDNA synthesis kit (Thermo Scientific). The template cDNA were then used for the amplification of BDNF and Cfos using SYBER green qPCR Master mix (Thermo Scientific). The relative gene expression was determined by comparing $2-\Delta\Delta Ct$ values normalized to β-actin.

Effects of Z-Acid Formulation I on Glutamate Levels on PTZ-Induced Acute Seizure in Rats Glutamate levels were also estimated in cortex and hippocampus following the administration of Z-acid formulation I. The glutamate levels were estimated using ELISA kit method (Bioassay Technology Laboratory, E1474Ra).

Sub-Chronic Toxicity Studies of Z-Acid Formulation I in Rats

Sub-chronic toxicity studies in rats were carried through intra-nasal route of administration. Rats were divided into two groups (n=4 per group). Test group was treated with Z-acid Formulation I through nasal route of administration (50 mg/kg). At the end of experiment, rats were sacrificed to collect the blood samples which were then processed to collect the serum. The serum samples were used to obtain LFT profile, kidney profile, protein, bilirubin, and triglycerides.

Experimental Findings
Results of Acute PTZ-Induced Seizure Model

Figure 1:
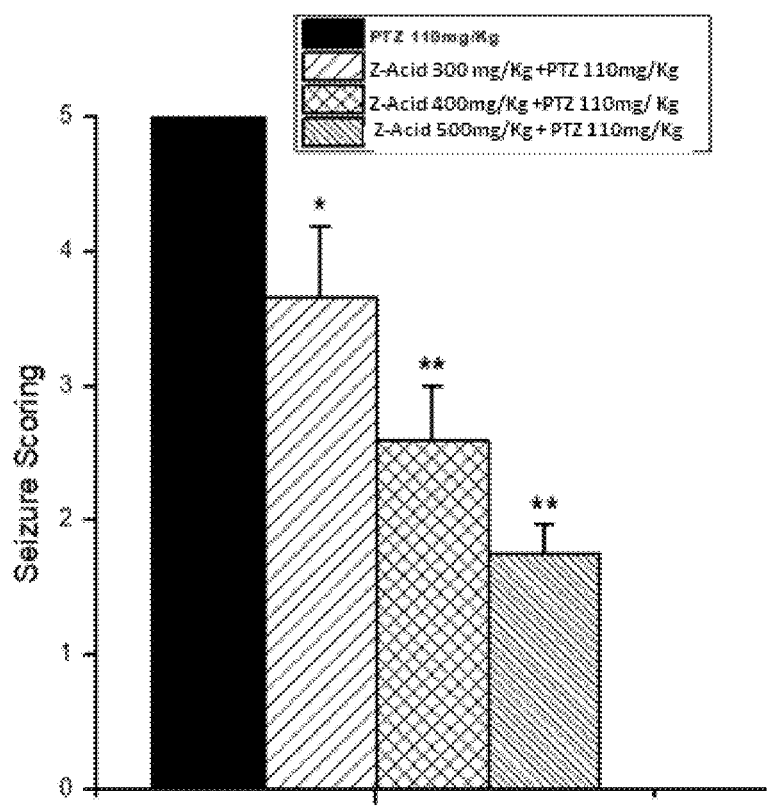
FIG. 1 depicts a Z-acid decreased seizure scores in acute model of PTZ-induce seizures. $P^* < 0.05$, $P^{**} < 0.01$) by applying One-Way ANOVA.

NMRI male mice weighing between 18-22 g were selected for the study. PTZ 110 mg/Kg was administered to the PTZ group and observed the first myoclonic jerk and HLTE. Z-acid was administered at a dose of 300 mg/Kg, 400 mg/Kg and 500 mg/Kg intraperitoneal to 3 different groups (n=6) and after 30 minutes, PTZ 110 mg/Kg was administered to these animals to evaluate the anti-seizure potential of the test compound at these doses. It was noted that Z-acid at all the three doses significantly delayed the onset of myoclonic seizure and prevented HLTE in all the animals compared to the PTZ group thus preventing the seizures in PTZ-induced seizure animal model (FIG. 1). The FIG. 1 shows that Z-acid derivative at a dose of 300 mg/Kg, 400 mg/Kg and 500 mg/Kg decreased the number seizure scoring significantly and dose dependently as compared to the PTZ group (n=5).

scPTZ-Induced Chemical Kindling Model of Epileptogenesis

A gradual increase in the seizure score was displayed reaching a score of 5 after 18 treatments by the untreated scPTZ control group animals with an average seizure score of 4.9. The valproic acid treated group compared to the PTZ-kindled control group did not exhibit any seizure pattern till the end of the kindling protocol. We observed that the active dose which was able to inhibit the process of epileptogenesis was 300 mg/kg body weight. At this test dose, Z-acid exhibited a complete inhibition in the development of kindling induced by scPTZ administration.

Toxicity Profile

Figure 2:
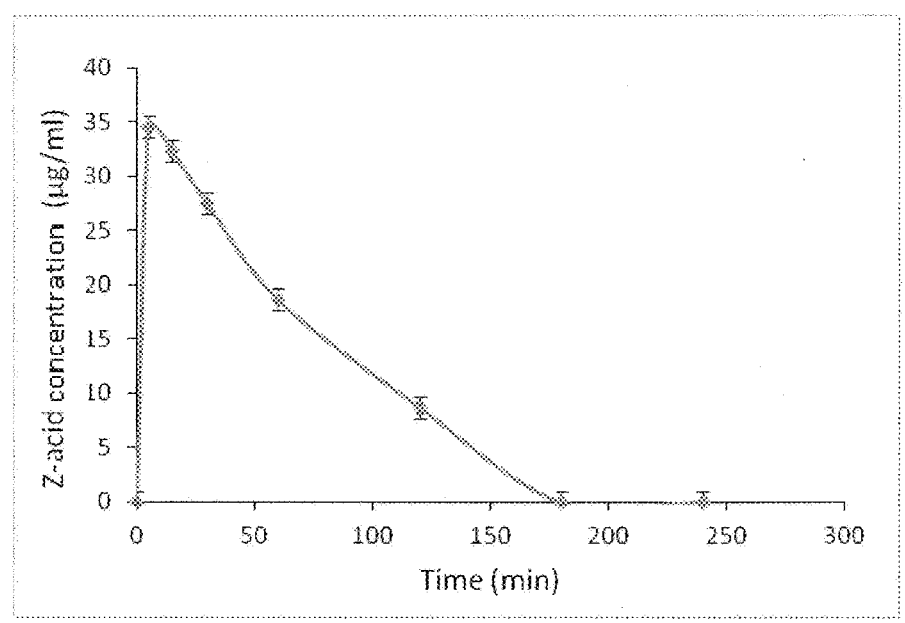
FIG. 2 depicts the level of Z-acid in plasma detected by GC/MS after intraperitoneal administration of Z-acid. Values are mean±SEM (n=4).
Figure 3:
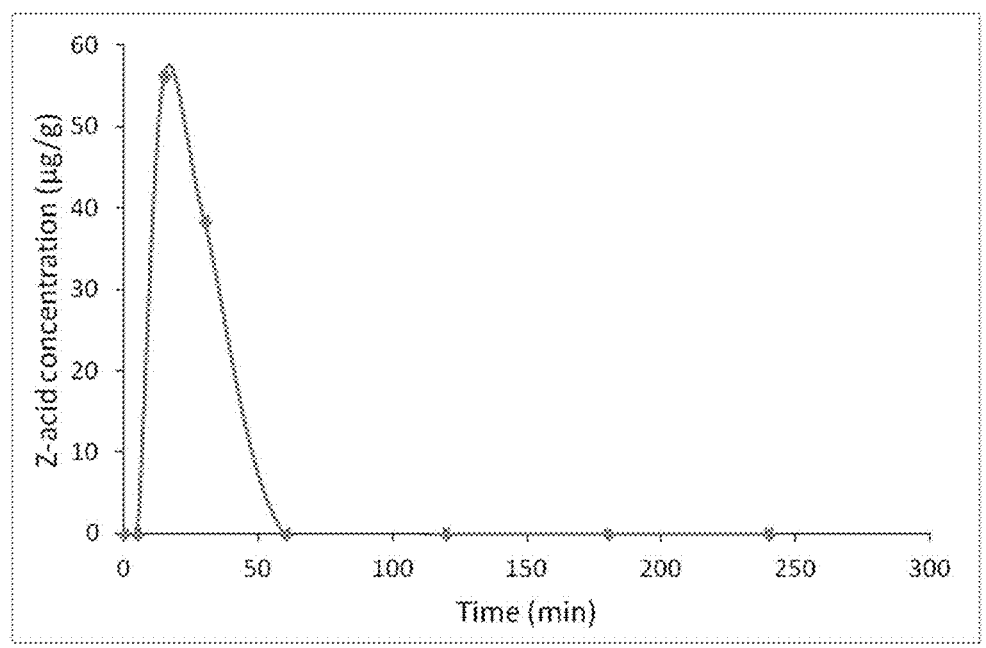
FIG. 3 depicts the graphical representation of Z-acid concentration detected in brain samples collected at different time points after intraperitoneal administration of Z-acid. Values are mean±SEM (n=4).

Sub-chronic toxicity studies were performed for 3 months, daily dosing of 300 mg/kg. All vital organs were intact, and no abnormal marks and spots were observed in gross examination. All animals survived until the end of experiments, Gross anatomy of the organs after treatment revealed no signs of toxicity. Blood samples were processed for LFT profile, CBC and LDH, creatinine, and urea levels which found in normal range after 3 months, daily dosing at the dose of 300 mg/kg Pharmacokinetics After intraperitoneal administration of Z-acid, plasma drug concentration was estimated through area of peak of the Z-acid obtained through GC/MS. The graph between plasma concentrations versus time was plotted. Similarly, brain Z-acid concentration was estimated by analyzing brain samples. It was observed that Z-acid rapidly appeared in both plasma and brain and peak concentration was achieved within 5 min and 15 min of intraperitoneal administration in plasma and brain, respectively. Thereafter, it rapidly disappeared from plasma (FIG. 2) and brain (FIG. 3) in parallel within 2-2.5 h and 1 h, respectively. Apparent volume of distribution was 10 L in plasma. The half-life was found to be 60 min in plasma. Thereafter, Z-acid was likewise eliminated in parallel from both compartments. No evidence was found for persistence or sequestration of Z-acid in brain.

Figure 4:
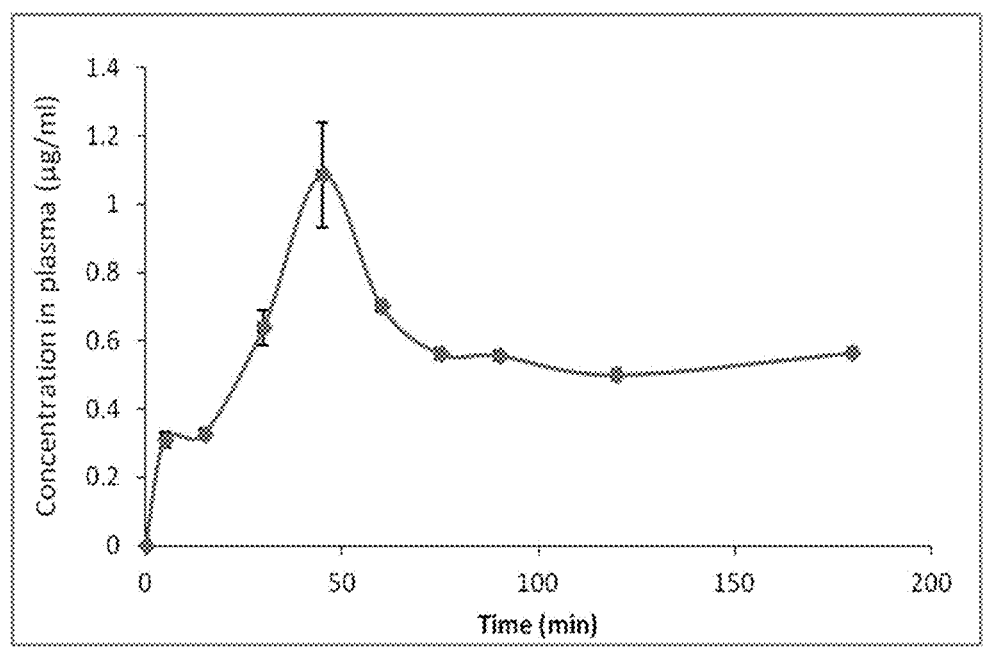
FIG. 4 depicts the graphical representation of Z-acid concentration detected by ultra-performance liquid chromatography (UPLC) in plasma samples at different time points collected after intra nasal administration of Z-acid formulation in rats. Values are mean±SEM (n=4).
Figure 5:
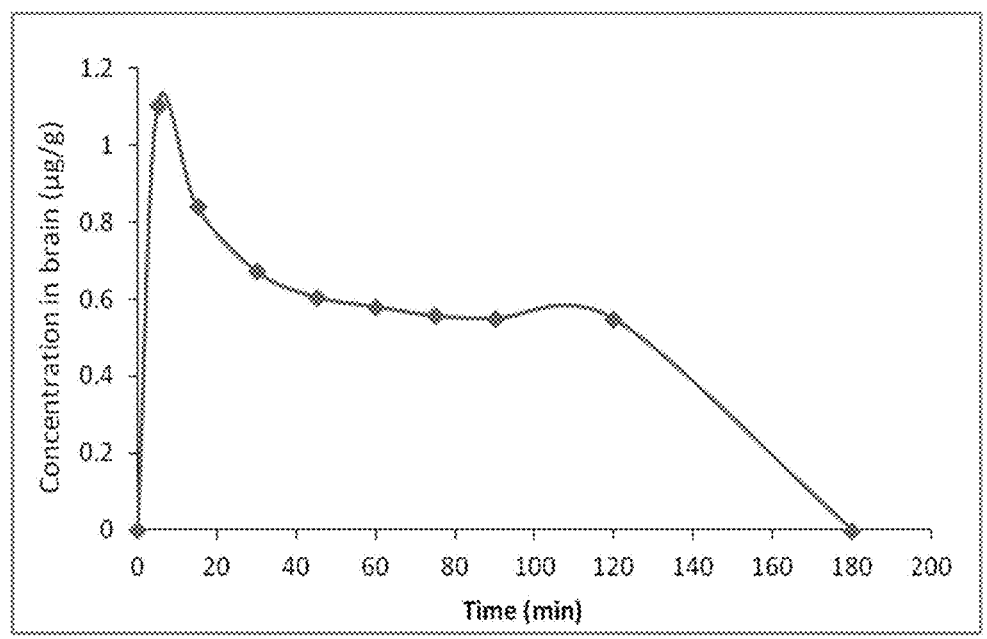
FIG. 5 depicts the graphical representation of Z-acid concentration detected by UPLC in brain samples at different time points collected after intra nasal administration of Z-acid formulation in rats. Values are mean±SEM (n=4).

Plasma drug concentration after intra nasal administration of Z-acid formulation was estimated through area of peak of the Z-acid obtained through UPLC. The graph between plasma concentrations versus time was plotted (FIG. 4). Similarly, brain Z-acid concentration was estimated by analyzing brain samples (FIG. 5). It was observed that Z-acid rapidly appeared in brain and peak concentration was achieved within 5 min of drug administration whereas in plasma the maximum concentration was obtained after 45 min of drug administration. The drug from brain was eliminated after 120 min whereas in plasma (FIG. 4) drug amount was still found after 180 min of nasal administration of drug. The plasma half-life through nasal route of administration was found to be 63 min.

Figure 6:
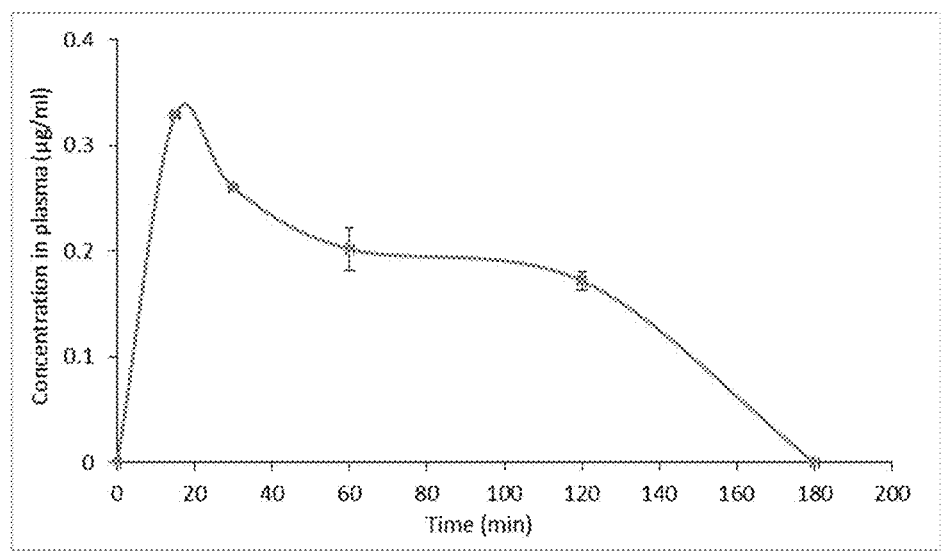
FIG. 6 depicts the graphical representation of Z-acid concentration detected by UPLC in plasma samples at different time points collected after intra nasal administration of Z-acid formulation in rabbits. Values are mean±SEM (n=4).

Plasma drug concentration after intra nasal administration of Z-acid Formulation I in rabbits was also estimated through area of peak of the Z-acid obtained through UPLC. The graph between plasma concentrations versus time was plotted (FIG. 6). Z-acid rapidly appeared in plasma and peak concentration was achieved within 15 min of drug administration. The plasma half-life through nasal route of administration was found to be 110 min.

Effects of Z-Acid on PTZ-Induced Epileptiform Activity in Rats Followed by Intraperitoneal Administration of Z-Acid (EEG Protocol)

Figure 7:
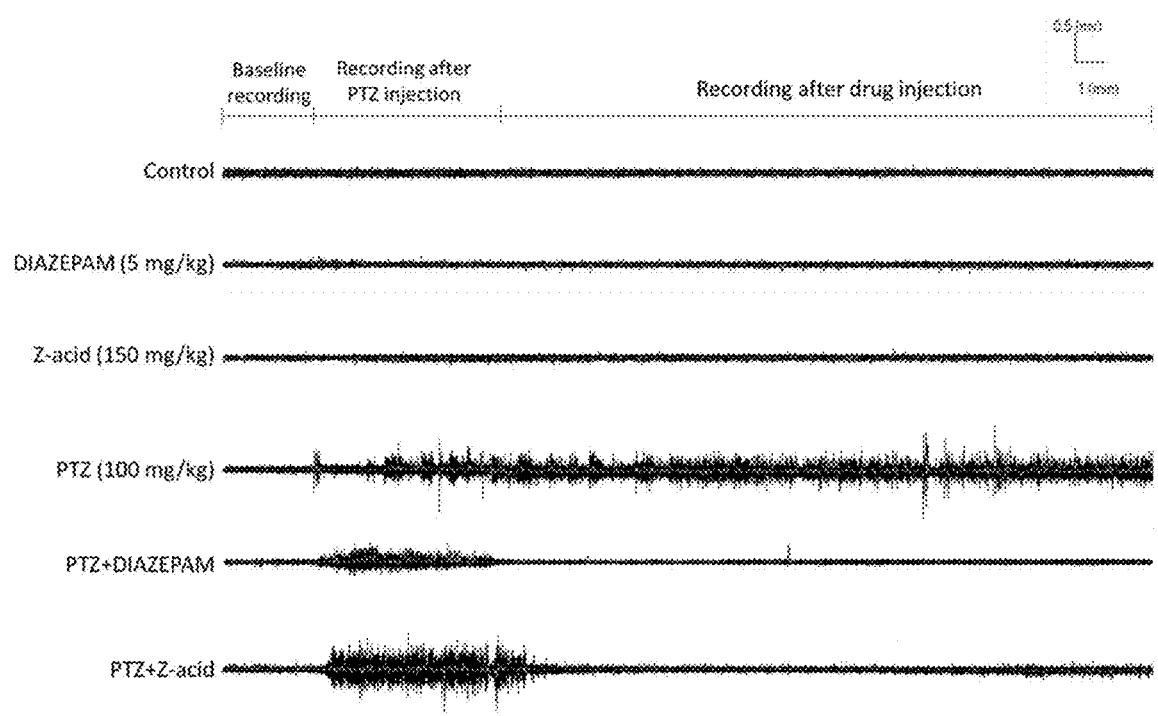
FIG. 7 depicts oscilloscope showing the effects of intraperitoneal administration of Z-acid on PTZ-induced epileptiform. Z-acid was injected after 10 min of PTZ injection.

Effects of intraperitoneal administration of Z-acid in animal model of PTZ-induced epileptiform. Seizures were monitored in term of spike discharge/min during three sessions of EEG recording including baseline, after PTZ injection and after drug injection. The drug was administered after 10 min of PTZ injection. It was observed that the spikes induced by PTZ was significantly reduced after 5 min of administering Z-acid (intraperitoneal) and then completely diminished after 7-10 min of Z-acid treatment. The recording was continued for 55 min from the start point. At the end of the experiment, number of spikes was counted from the oscilloscope with the help of e-probe software manufactured by Science beam Institute, Iran. The data was collected from three time points of experiments including baseline, PTZ injection and compound injection (FIG. 7). Statistical analysis showed a significant increase in spike discharge in PTZ animals as compared to control animals (P<0.01). However, the spike discharge was significantly reduced by diazepam and Z-acid administration in PTZ+diazepam, PTZ+Z-acid groups, respectively, as compared to PTZ-injected animals (P<0.01) (FIG. 8).

Figure 8:
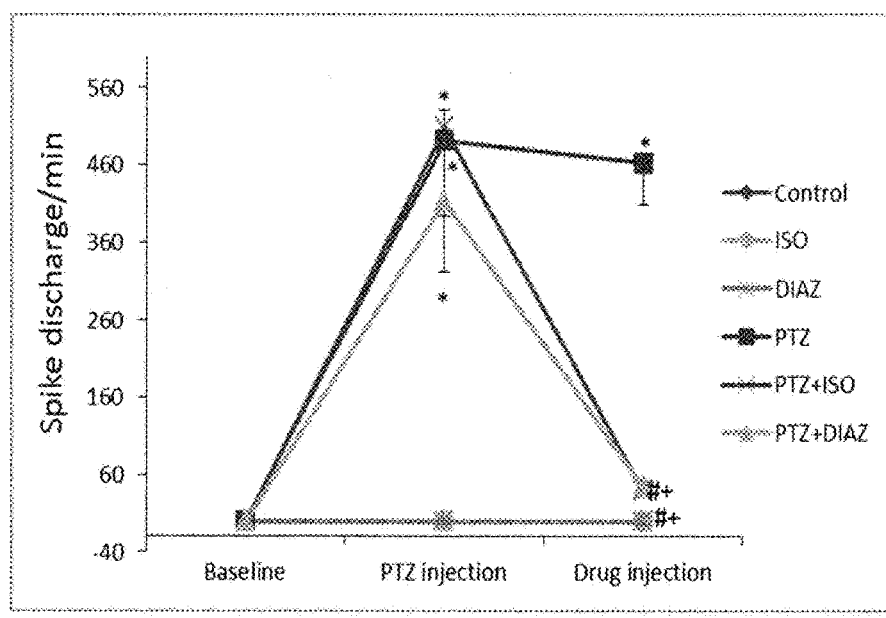
FIG. 8 depicts the effects of intraperitoneal administration of Z-acid in animal model of PTZ-induced epileptiform.

In FIG. 8, values are mean±SEM (n=6). Significance was observed using Bonferroni test *P<0.01 as compared to baseline reading; +P<0.01 as compared to the recording after PTZ injection; #P<0.01 as compared to PTZ group for respective session.

PTZ-Induced Epileptiform Activity in Rats Followed by Intranasal Application of Z-Acid Formulation (EEG Protocol)

Figure 9:
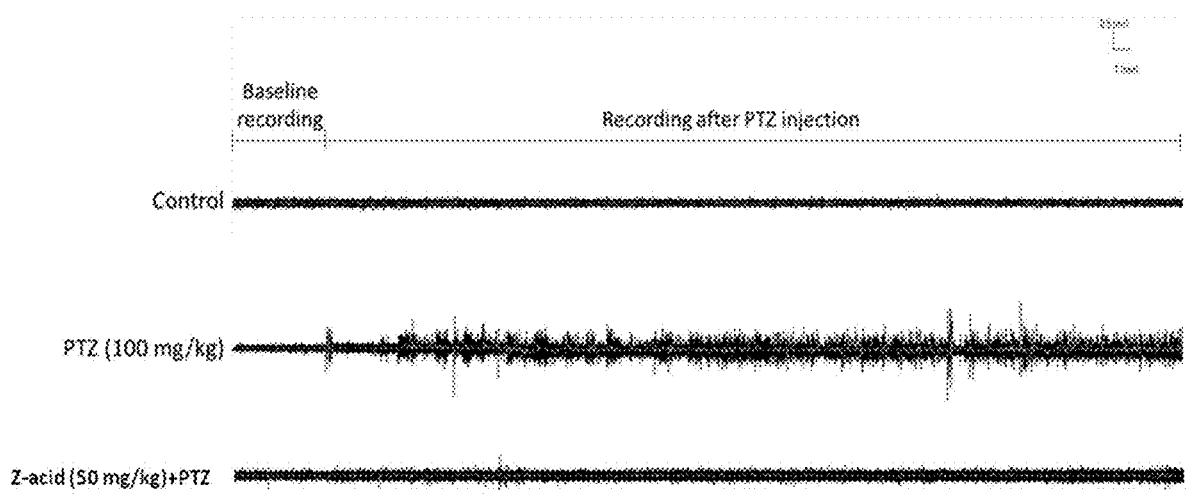
FIG. 9 depicts oscilloscope showing the effects of Z-acid formulation administered through nasal route on PTZ-induced epileptiform. Z-acid was administered before 30 min of PTZ injection.

Effect of intranasal administration of Z-acid formulation in animal model of PTZ-induced epileptiform was studied. Seizures were monitored in term of spike discharge/min. The drug was administered before 30 min of PTZ injection. The recording continued for 55 min from the start of experiment (FIG. 9). At the end of experiment, number of spikes was counted from the oscilloscope with the help of e-probe software manufactured by Science beam Institute, Iran. Statistical analysis showed a significant increase in spike discharge in PTZ animals as compared to control animals (P<0.01). However, the spike discharge was significantly reduced by intranasal administration of Z-acid administration in Z-acid+PTZ as compared to PTZ-injected animals (P<0.01). The results are summarized in FIG. 10.

Figure 10:
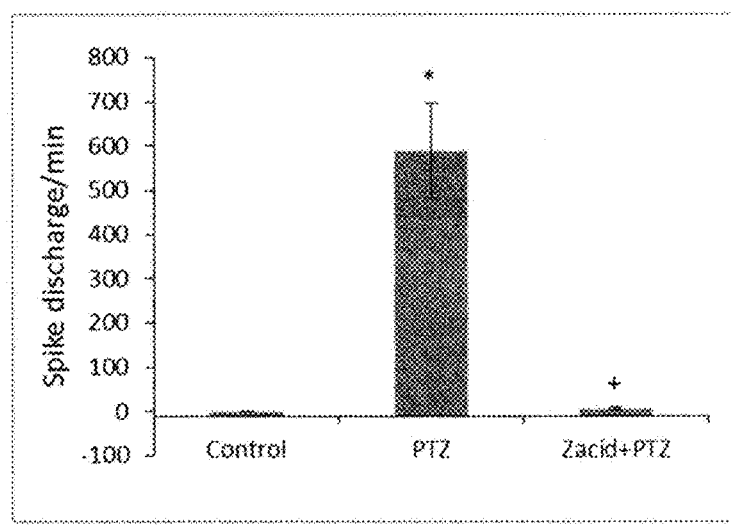
FIG. 10 depicts the effects of intranasal administration of Z-acid formulation in an animal model of PTZ-induced epileptiform.

In FIG. 10, values are mean±SEM (n=6). Significance was observed using Tukey's test *p<0.01 as compared control animals; +p<0.01 as compared PTZ group.

Figure 11:
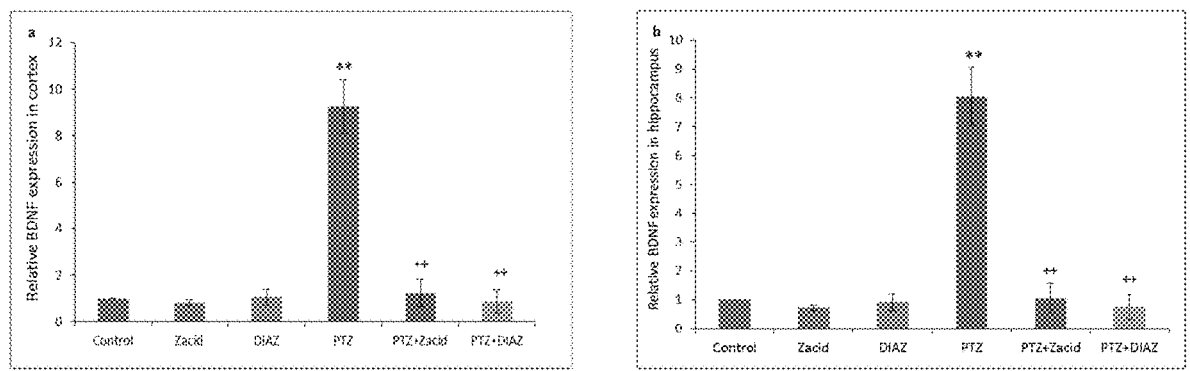
FIG. 11 Effects of intraperitoneal administration of Z-acid and diazepam on gene expression of BDNF in PTZ-induced rat model of acute seizure observed in cortex (a) and hippocampus (b). Values are mean±SEM (n=3). Statistical significance was obtained by two-way ANOVA followed by Bonferroni post-hoc test $**p < 0.01$ as compared control animals; $++p < 0.01$ as compared PTZ group.
Figure 12:
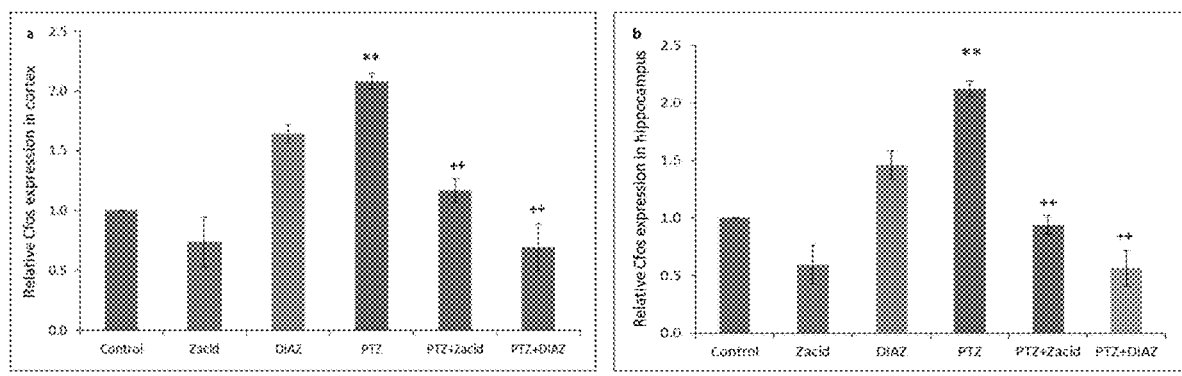
FIG. 12 Effects of intraperitoneal administration of Z-acid and diazepam on gene expression of cfos in PTZ-induced rat model of acute seizure observed in cortex (a) and hippocampus (b). Values are mean±SEM (n=3). Statistical significance was obtained by two-way ANOVA followed by Bonferroni post-hoc test $**p < 0.01$ as compared control animals; $++p < 0.01$ as compared PTZ group.

Effects of Z-Acid Formulation I on BDNF and Cfos Gene Expression on PTZ-Induced Acute Seizure in Rats Intraperitoneal Experiment Two-way ANOVA showed significantly increased (p<0.01) expression of BNDF (FIG. 11a and 11b) and c-fos (FIGS. 12 and 12b) in PTZ treated rats as compared to control animals in both cortex and hippocampus regions. The increased BDNF and Cfos levels were significantly reduced following the treatment (i.p) of Z-acid (p<0.01) and diazepam (p<0.01) as compared to the rats injected with PTZ alone and become comparable to control animals.

Intranasal Experiment

Figure 13:
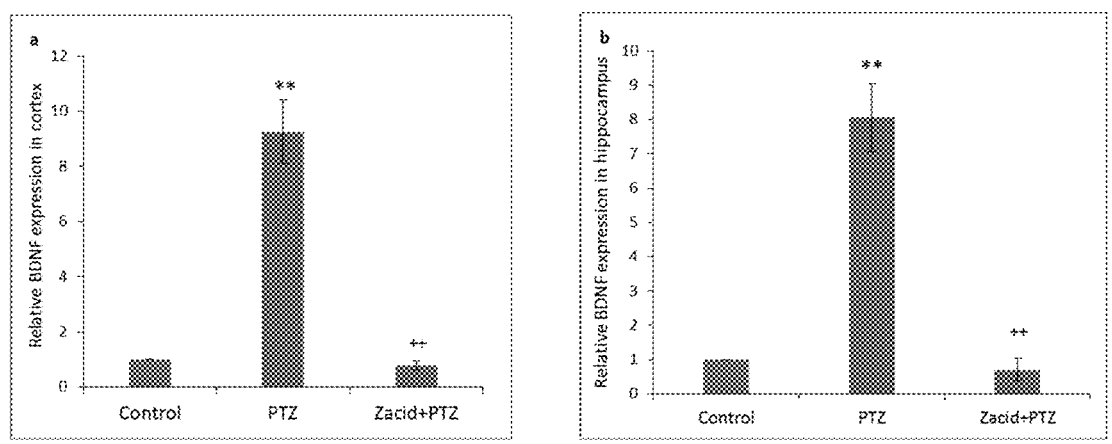
FIG. 13 Effects of intranasal administration of Z-acid formulation and diazepam on gene expression of BDNF in PTZ-induced rat model of acute seizure observed in cortex (a) and hippocampus (b). Values are mean±SEM (n=3).

Statistical analysis by one-way ANOVA showed that administration of PTZ significant increased (p<0.01) gene expression of BNDF (FIGS. 13a and 13b) and cfos (FIGS. 14a and 14b) in both investigated brain regions. Whereas in rats which were pre-treated with Z-acid intranasal, gene expression of BNDF and Cfos was significantly reduced as compared to PTZ treated animals (p<0.01).

Effects of Z-Acid Formulation I on Glutamate Levels on PTZ-Induced Acute Seizure in Rats Intraperitoneal Experiment Two-way ANOVA showed significantly increased (p<0.01) glutamate levels (FIG. 15a and FIG. 15b) in PTZ treated rats as compared to control animals in both cortex and hippocampus regions. The increased glutamate levels were significantly reduced following the treatment of Z-acid (p<0.01) and diazepam (p<0.01) as compared to the rats injected with PTZ alone and become comparable to control animals.

Intranasal Experiment

Statistical analysis by one-way ANOVA showed that administration of PTZ significant increased (p<0.01) glutamate levels (FIGS. 16a and 16b) in both investigated brain regions. Whereas in rats which were pre-treated with Z-acid glutamate levels were significantly reduced as compared to PTZ treated animals (p<0.01).

Sub-Chronic Toxicity Studies of Z-Acid Formulation I in Rats

Sub-chronic toxicity studies in rats were carried through intra-nasal route of administration. Rats were divided into two groups (n=4 per group). The serum samples were used to obtain LFT profile, kidney profile, protein, bilirubin, and triglycerides. These biochemical parameters were found in normal range after 3 months of daily intra-nasal dosing (50 mg/kg) (FIGS. 17-19).

What is claimed is:

1. A method of treating epilepsy by administering through a nasal route, an effective amount of a compound (Z)-2-(3,5,5-trimethyl-2-cyclohexen-1-ylidene) acetic acid or its salts, in a suitable pharmaceutical formulation to humans in need of treatment.

2. A method of treating epilepsy by administering through a nasal route, an effective amount of a compound (Z)-2-(3,5,5-trimethyl-2-cyclohexen-1-ylidene)-Lys-Lys-OH or its salts, in a suitable pharmaceutical formulation to humans in need of treatment.

* * * * *